United States Patent
Paltieli et al.

(10) Patent No.: US 8,043,233 B2
(45) Date of Patent: Oct. 25, 2011

(54) METHOD FOR MONITORING ORIENTATION OF A MATERNAL PELVIS

(75) Inventors: Yoav Paltieli, Haifa (IL); Reuven Lewinsky, Kiryat Tivon (IL)

(73) Assignee: Trig Medical Ltd, Yokneam Ilit (IL)

( * ) Notice: Subject to any disclaimer, the term of this patent is extended or adjusted under 35 U.S.C. 154(b) by 624 days.

(21) Appl. No.: 11/571,274

(22) PCT Filed: Feb. 13, 2005

(86) PCT No.: PCT/IL2005/000183
§ 371 (c)(1), (2), (4) Date: Dec. 26, 2006

(87) PCT Pub. No.: WO2005/077261
PCT Pub. Date: Aug. 25, 2005

(65) Prior Publication Data
US 2008/0234581 A1    Sep. 25, 2008

(51) Int. Cl.
*A61B 5/103* (2006.01)

(52) U.S. Cl. ........ 600/588; 600/424; 600/304; 600/437; 600/438; 600/443; 600/591

(58) Field of Classification Search .................. 600/588, 600/304, 424, 425, 426, 437, 438, 587, 591, 600/443
See application file for complete search history.

(56) References Cited

U.S. PATENT DOCUMENTS
5,935,061 A * 8/1999 Acker et al. .................. 600/304
2003/0114779 A1 * 6/2003 Paltieli .......................... 600/588
* cited by examiner

*Primary Examiner* — Brian Casler
*Assistant Examiner* — Amanda Lauritzen
(74) *Attorney, Agent, or Firm* — Dekel Patent Ltd.; David Klein

(57) ABSTRACT

A method wherein a location or position sensor cooperates with a controller or other operating system such that a predefined motion pattern (circular motion, double click, translatory motion, reciprocal motion, and the like, and any combination thereof) of the sensor performs one or more specific tasks, which are not necessary related to the spatial locations per se of the sensor. Also a method for identifying sensors and landmarks is described including sensing the present location of the sensor plus an additional point and comparing with locations in the recent past.

4 Claims, No Drawings

METHOD FOR MONITORING ORIENTATION OF A MATERNAL PELVIS

FIELD OF THE INVENTION

The present invention relates generally to methods for performing one or more specific tasks, such as instructing a computerized system to perform actions, using a predefined motion pattern of a sensor. Non-limiting examples of such tasks can include identifying sensors and/or landmark locations on objects, such as in sensing, monitoring, measuring and/or diagnosing various objects and/or phenomena.

BACKGROUND OF THE INVENTION

There are many applications that require some sort of confirmation to a system that sensors have been placed properly on objects for different purposes, such as sensing, monitoring, measuring or diagnosing. For example, temperature sensors, such as thermocouples or thermistors, may be placed on an internal combustion engine to provide a thermal mapping of the engine. Biosensors, such as pulse sensors, blood pressure sensors, $CO_2$ sensors, etc., may be placed on a patient to monitor various activities, such as heart function, breathing, perspiration, etc.

One important example of a medical application that requires placing sensors on objects and which takes into account the spatial position of the sensor or of some landmark location (e.g., some anatomical part) is that of monitoring the progress of labor during childbirth. Applicant's U.S. Pat. No. 6,200,279, entitled "Method And Apparatus For Monitoring The Progress Of Labor", describes such an application. Briefly, in one of the methods described in U.S. Pat. No. 6,200,279, a position sensor is attached to a predetermined point on the mother's pelvic bones, and the location of the position sensor in three-dimensional space is monitored relative to a reference. The location of a fetal presenting part (e.g., the tip or the bi-parietal diameter (BPD) of the fetal head) may be monitored with respect to the predetermined point on the mother's pelvic bones to provide an indication of the progress of labor. Not only may position sensors be used to monitor the location of the fetal presenting part, but they may also be used to monitor the position of the sides of the mother's uterine cervix.

If more than one sensor is used, it is readily understood that each sensor must be properly identified. Various methods are known in the art for identifying the abovementioned sensors. For example, independent external verification signals have been used to identify sensors.

SUMMARY OF THE INVENTION

The present invention seeks to provide improved and simplified methods for instructing systems to perform certain tasks, such as identifying sensors and/or landmark locations, as is described more in detail hereinbelow.

DETAILED DESCRIPTION OF EMBODIMENTS

In accordance with an embodiment of the present invention, a sensor, such as but not limited to a position or location sensor, may cooperate with a controller or other operating system such that a predefined motion pattern (circular motion, double click, translatory motion, reciprocal motion, and the like, and any combination thereof) of the sensor performs one or more specific tasks, which are not necessary related to the spatial locations per se of the sensor.

In accordance with an embodiment of the present invention, a known motion pattern of the sensor, such as but not limited to, a position sensor, with respect to its surroundings may be used to identify the sensor. For example, in a system that uses many sensors, the first sensor may be identified by moving it in a triangular pattern, the second sensor may be moved in a crisscross pattern, the third sensor in a rectangular pattern, and the like.

Another possible embodiment is the use of a "double touch event" to identify the sensor or landmark. For example, the system may keep a history of the sensor locations. The present location of the sensor plus an additional point (e.g., some anatomical part, object, or another sensor or another landmark, such as a stationary sensor, one which did not perform a motion greater than X cm at the last Y minutes) may be measured and compared with locations in the recent past (e.g., in the last two seconds). The location of the sensor may be measured by the sensor itself if the sensor is a position sensor; otherwise another position sensor may be used to measure the position of the sensor being identified.

In one example, two measurements of the position of the sensor being identified are taken within a predetermined time period (e.g., within two seconds), these being the "present" and the "recent past" measurements. Likewise, two measurements of the additional point are taken within a predetermined time period (not necessarily the same period of time). If the "present" and the "recent past" measured positions of the sensor being identified fall with a predetermined area, e.g., circle (e.g., not greater than 5 mm diameter), plus the "present" and the "recent past" measured positions of the additional point fall with a predetermined circle (which could be a different diameter, such as but not limited to, 4 cm), then the sensor being identified is considered positively and unambiguously identified.

In accordance with an embodiment of the present invention, the method may be used to automatically identify any sensor being currently used for a specific task in a multisensor system.

In accordance with another embodiment of the present invention, the method may be used to automatically identify completion of a step or process in a multi-step workflow. The completion of the step may be identified by double-touching a landmark or sensor, as described above.

The invention has many applications, such as but not limited to, tracking locations of sensors in tracker-based systems which measure anatomic features or phenomena (such as in U.S. Pat. No. 6,200,279), tracking locations of sensors in tracker-based systems which perform guided interventional procedures (e.g., surgery, ablation, biopsy and the like), and systems that require registration between physical points on a body and pre-acquired images or models.

Other exemplary, non-limiting applications of the invention include a position sensor mounted on a pilot helmet sight. The position sensor may be mounted on the helmet for automatically aiming a weapon to a target, to which the pilot head is aimed. In an embodiment of the present invention, a predefined motion pattern of the helmet-mounted sensor (e.g., nodding the head "yes" or "no") may cause some action related to the pilot computer screen, such as "enter" or "next screen" or "delete" and so on.

As another example, a personal computer may be provided with a position or motion sensor. The predefined motion pattern of the position or motion sensor may be used to instruct the computer to perform an action that in the prior art would require maneuvering an input device, such as a mouse or keys of a keyboard.

As yet another example, a key to open a safe, lock box, safety deposit box or other lockable security item may be provided with a position or motion sensor. The lockable security item may be provided with a controller that interprets a predefined motion pattern of the position or motion sensor. Upon recognition and validation of the predefined motion pattern, the controller may permit opening the lockable security item.

As mentioned above, one of the many applications of the invention is in tracking locations of sensors which measure anatomic features or phenomena. A non-limiting example of such an application is now described, this being a method for the determination of fetal head station during labor by ultrasound imaging of the fetal head tip and relating it to the maternal pelvic inlet.

The maternal pelvis may be modeled, constructed and positioned according to previously described methods in the art (such as in U.S. Pat. No. 6,200,279). The birth canal may be added to the existing pelvic model. After performing external pelvimetry, the subject's pelvis may be reconstructed using a standard pelvic model. Positioning of the birth canal may be done according to textbook definitions describing its curvature within the pelvis.

A position sensor may be attached to an ultrasonic (US) transducer as previously described for BPD (bi-parietal diameter) plane measurement (such as in U.S. Pat. No. 6,200,279). In the new method, while holding the US transducer above the pubic bone, the user may scan the fetal skull from the pelvic inlet plane downwards to form US images. At each level, the birth canal center or area may be projected upon the US image. The user may move the transducer to the point where the skull may be still visible, while aiming to align the skull contour with the birth canal mark. At that level, the US image may be frozen and a measurement may be taken. Assuming a fixed distance between the fetal head tip and the BPD plane, or if the BPD plane was visualized at an early stage of labor and the tip-BPD distance was calculated, fetal head station can then be calculated.

Fetal head station can also be determined in a similar mode by performing a trans-perineal, trans-labial or a trans-vaginal US. Again, the birth canal may be projected on the US image but the scanning direction may be adapted to the different location of the US transducer starting from a downward direction and moving up until the fetal skull contour appears.

In both approaches, fetal head station can be either related to the pelvic inlet plane calculated from pelvimetry data or to the ischial spines if these have been sampled during internal pelvimetry.

Methods are known for reconstructing maternal bony pelvis by touching four known landmarks (see, for example, U.S. Pat. No. 6,669,653 to Paltieli). New methods are now described for accomplishing the same by touching only one to three bony landmarks. Furthermore, a method will be described for accomplishing the same, or at least for the determination of the spatial location of the pelvic inlet plane, by touching only one bony landmark of the maternal pelvis.

(It is noted that one of the known positions mentioned below might be the reference sensor if attached to a known location on the pelvis.)

As is known in the art, once the maternal pelvis has been reconstructed from an external (four or more point) pelvimetry, and as long as a reference sensor is attached to a fixed point on the pelvis, movement and change of position of the pelvis can be continuously monitored. In case a certain maternal movement (e.g., flexure of the hips) has caused a change in the angular position of the reference sensor on the pelvis, touching 2-3 landmarks of the pelvis can update the system on the real new position of the pelvis.

Assuming the mother's pelvis is lying straight on the delivery bed (both hips equidistant from the bed and the head-feet axis is parallel to the long axis of the bed), by having the reference sensor in place and by touching one known point, preferably in the midline (i.e. pubic bone), the system can update the new pelvic position.

If one assumes a significant similarity between the pelvises of different women, then the angle between a plane common to the two anterior superior iliac spines and the pubis and the pelvic inlet plane is almost constant. The location and position of the pelvis and the pelvic inlet plane can then be calculated from the 2-3 known points only.

If one assumes that the plane of the delivery bed and its relation to the transmitter are known, then by having the reference sensor on one known position of the pelvis (e.g., anterior superior iliac spine) and by touching one other known point (e.g., the pubis), a standard pelvis can be reconstructed and the pelvic inlet plane positioned within it.

The following is a method for creating 2D and 3D images of the fetal head based on the identification of different landmarks of the fetal head:

1. By marking one or more anatomical landmarks on the fetal head, the position of which may be well defined on a standard fetal head model, e.g. eye(s), cervical spine close to the skull, etc., the image of the head can be brought (rotated) to the correct orientation (position) which can be presented in a 2D image.

2. The tip (lowermost point) of the fetal head can be either identified by US as described above or its location measured by touching it with a position sensor. This provides the information for placing the fetal head image in the correct height (station) within the pelvis.

3. The combination of station and position provides the complete data for correct 3D presentation of the fetal head within the maternal pelvis.

What may be claimed is:

1. A method for monitoring orientation of a maternal pelvis, comprising:
   obtaining a location in three-dimensional space of a fixed, known point on a maternal pelvis of a woman relative to a reference, said woman lying on a bed; and
   monitoring a change in orientation of the maternal pelvis after movement of the maternal pelvis by tracking just two points, comprising the following steps:
   a) after said maternal movement, obtaining a location in three-dimensional space of another point on the maternal pelvis of the woman relative to a reference;
   b) assuming two assumptions: (1) the maternal pelvis is lying straight on the bed, with both hips of the woman equidistant from a head of the woman and also equidistant from the bed; and (2) there is an almost constant angle between a plane common to the woman's iliac spines, pubis and pelvic inlet plane;
   c) calculating a new location and position of the pelvis and the pelvic inlet plane as a function of a spatial relationship of just two points, namely said one other point on said pelvis with respect to said fixed, known point and with respect to said angle; and
   d) calculating fetal head station based on a distance between a bi-parietal diameter (BPD) plane or a known point of a fetal head and said new location and position of the pelvic inlet plane.

2. The method according to claim 1, wherein obtaining the locations in three-dimensional space of the fixed, known point and of the other point comprises touching said points with a position sensor attached to an ultrasonic transducer.

3. The method according to claim 1, wherein obtaining the locations in three-dimensional space of the fixed, known point and of the other point comprises obtaining the locations from an ultrasonic image.

4. The method according to claim 1, wherein said other point is on the pubis and said fixed, known point is superior to the pubis.

* * * * *